United States Patent
Konings et al.

(10) Patent No.: US 6,579,919 B2
(45) Date of Patent: Jun. 17, 2003

(54) DENTAL TRY-IN PASTES, KITS, AND METHODS

(75) Inventors: Mark S. Konings, Minneapolis, MN (US); Edward J. Winters, North St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/952,583

(22) Filed: Sep. 12, 2001

(65) Prior Publication Data

US 2003/0069325 A1 Apr. 10, 2003

(51) Int. Cl.[7] .................. A61K 6/083; A61C 5/04
(52) U.S. Cl. .................. 523/118; 523/115; 523/116; 433/226; 433/228.1; 433/215
(58) Field of Search .................. 523/115, 116, 523/118; 433/34, 36, 50, 201.1, 226, 228.1

(56) References Cited

U.S. PATENT DOCUMENTS

| 4,503,169 A | 3/1985 | Randklev |
| 6,030,606 A | 2/2000 | Holmes |

FOREIGN PATENT DOCUMENTS

| JP | 59 134705 | 1/1993 |

OTHER PUBLICATIONS

"Polyethylen Glycol", #20, 240–1, Aldrich Catalog p. 1244, 1988.*
"Calibra® Cements and Liners," Dentsply U.S. product catalog [online]. Dentsply, York, PA (2002).
"Introducing Nexus2 For Creating Masterpieces of Modern Esthetic Dentistry," product brochure [online]. Kerr Dentistry, Orange, CA (2001).
"3M ESPE RelyX™ Veneer Cement System Technical Product Profile" Technical Product Brochure, 3M Dental Products, St. Paul, MN; title page, publication page, table of contents and pp. 4–22; 2001.
"Variolink® II," product brochure [online]. Ivoclar Vivadent, Amherst, NY (2002).
"Calibra™ Try–In Pastes," material safety data sheet. Dentsply, Milford, DE (Mar. 8, 1999); 2 pgs.
"Variolink® II Try–In–Paste," material safety data sheet [online]. Ivoclar Vivadent Inc., Amherst, NY.

* cited by examiner

*Primary Examiner*—Tae H Yoon
(74) *Attorney, Agent, or Firm*—Doreen S. L. Gwin

(57) ABSTRACT

A try-in paste, kit, and method of use, wherein the try-in paste includes: a polyalkylene glycol that is liquid at room temperature; a polyalkylene glycol that is solid at room temperature; and a particulate material; wherein the polyalkylene glycols are present in amounts to provide a paste having a consistency of about 20 mm to about 50 mm; and wherein the particulate material is present in an amount to provide a try-in paste of a shading that matches the shading of a corresponding polymerized dental cement.

13 Claims, No Drawings

DENTAL TRY-IN PASTES, KITS, AND METHODS

FIELD OF THE INVENTION

The present invention describes a paste with application as a try-in paste (i.e., trial paste) useful for assisting in the determination of the correct choice of a dental cement used to apply a dental prosthesis to a tooth.

BACKGROUND

Try-in pastes (i.e., trial pastes) are used in assisting a dentist in the selection of an appropriate dental cement for bonding a dental prosthesis (e.g., veneer, in-lay, on-lay, etc.), which is often translucent, to a tooth. This selection depends on the optical properties of the final polymerized cement and the dental prosthesis compared to the optical properties of the other teeth of the patient.

Typically, a try-in paste, which is matched to a dental cement with respect to optical properties (often just color-matched), is used to apply temporarily the dental prosthesis to a prepared tooth surface. The dentist determines if the optical properties (at least color) would be esthetically desirable for the combination of the prosthesis and underlying cement. If so, the prosthesis is removed and try-in paste is washed away and the appropriately matched dental cement is used to apply the prosthesis. If not, the prosthesis is removed and try-in paste is washed away and this is repeated with a different try-in paste appropriately matched to a different dental cement.

Traditionally, such try-in pastes are based on glycerin. They typically either have poor handling characteristics or leave a residue after water cleanup. Additionally, because glycerin is transparent optically, some difficulty is encountered in preparing pastes whose optical properties closely match those of the polymerized cement. Thus, additional try-in pastes are desired that are capable of better shade matching.

SUMMARY OF THE INVENTION

The present invention provides a try-in paste (i.e., trial paste) suitable for shade matching to a corresponding polymerized dental cement, so that a dental cement of the correct shade can be selected for bonding a dental prosthesis to a tooth of a patient. As used herein, "shade matching" refers to the use of a try-in paste for guiding a dentist in the selection of a shade-matched dental cement for use in bonding a dental prosthesis to a tooth of a patient. The selection of an appropriate dental cement shade depends on the optical properties (typically, color, and preferably, color and opacity) of the polymerized cement and the dental prosthesis compared to the optical properties of the other teeth of the patient.

In a preferred embodiment, the present invention provides try-in paste that includes: a polyalkylene glycol that is liquid at room temperature; a polyalkylene glycol that is solid at room temperature; and particulate material; wherein the polyalkylene glycols are present in amounts to provide a paste having a consistency of about 20 mm to about 50 mm; and wherein the particulate material is present in an amount to provide a try-in paste having a shading (i.e., shade) that matches the shading of a corresponding polymerized dental cement.

Preferably, the shading match includes a color match, and more preferably, a color match and an opacity match. That is, for particularly preferred embodiments, particulate material is present in an amount to provide a try-in paste having a color and opacity that matches the color and opacity of a corresponding polymerized dental cement. Preferably, the color match is within a Delta E* of three units or less. Preferably, the shading match is within a Delta CR of five units or less.

Preferably, the polyalkylene glycols are polyethylene glycols. Preferably, the liquid polyethylene glycol has a weight average molecular weight of about 100 g/mol to about 600 g/mol and the solid polyethylene glycol has a weight average molecular weight of about 700 g/mol to about 20,000 g/mol. Preferably, the ratio of liquid to solid PEG is within a range of about 1/1 to about 10/1, and more preferably, about 2/1 to about 5/1.

In another preferred embodiment, the present invention provides a kit for selecting a dental cement for bonding a dental prosthesis to a tooth of a patient. The kit includes: a dental cement; and a corresponding try-in paste, wherein the try-in paste is as described above. The kit typically and preferably includes more than one try-in paste and their corresponding cements. The try-in paste includes particulate material in an amount to provide a try-in paste having a shading that matches the shading of a corresponding polymerized dental cement. Preferably, the shading match between the try-in paste and the corresponding polymerized dental cement includes a color match and an opacity match. Preferably, the color match is within a Delta E* of three units or less. Preferably, the opacity match is within a Delta CR of five units or less.

Another preferred kit includes a dental cement and a corresponding try-in paste, wherein the try-in paste includes: a polyethylene glycol that is liquid at room temperature and has a weight average molecular weight of about 100 g/mol to about 600 g/mol; a polyethylene glycol that is solid at room temperature and has a weight average molecular weight of about 700 g/mol to about 20,000 g/mol; and particulate material that includes a pigment and an optional filler; wherein the polyethylene glycols are present in amounts to provide a paste having a consistency of about 20 mm to about 50 mm; wherein the particulate material is present in an amount to provide a try-in paste having a shading that matches the shading of a corresponding polymerized dental cement.

The present invention also provides a method of selecting a dental cement for bonding a dental prosthesis to a tooth of a patient. The method includes: selecting a first try-in paste; applying the dental prosthesis to the tooth of the patient using the first try-in paste; comparing the shading of the dental prosthesis and the first try-in paste to the shading of the other teeth of the patient to determine if there is an appropriate match; removing the first try-in paste; and bonding the dental prosthesis to the tooth using a corresponding dental cement. The try-in paste includes: a polyalkylene glycol that is liquid at room temperature; a polyalkylene glycol that is solid at room temperature; and particulate material; wherein the polyalkylene glycols are present in amounts to provide a paste having a consistency of about 20 mm to about 50 mm; wherein the particulate material is present in an amount to provide a try-in paste having a shading that matches the shading of a corresponding polymerized dental cement. Preferably, comparing the shading includes comparing the color and opacity of the dental prosthesis and the try-in paste to the color and opacity of the other teeth of the patient. Preferably, the method further includes selecting a different try-in paste if the match using the first try-in paste is not appropriate.

DETAILED DESCRIPTION OF PREFERRED EMBODIMENTS

This invention provides dental try-in (i.e., trial) pastes that include a mixture of liquid and solid polyalkylene glycols, preferably, polyethylene glycols (PEGs). Such try-in pastes are used to shade match (typically, match the color, and preferably match the color and opacity) of final polymerized dental cements used to apply a dental prosthesis (i.e., restorative such as a veneer, in-lay, on-lay, etc., whether it be made of porcelain, ceramic, or a composite material). The dental cements typically can be resin cements, ionomeric cements, or resin-modified ionomeric cements. Preferably, the present try-in pastes are used to match the optical properties of (meth)acrylate-based resin cements.

Such pastes have a consistency (defined below) such that they are semi-solid. Such properties provide good handling characteristics (e.g., little or no slump). Preferred pastes are homogeneous. Preferred pastes are also shelf-stable such that there are no significant changes in handling, homogeneity, color, or opacity while stored at room temperature in the dark for at least one year, and preferably for at least two years. Alternatively, preferred pastes are stable such that there are no significant changes in handling, homogeneity, color, or opacity while stored overnight in the dark at 37° C., and preferably at 45° C.

The pastes are preferably removable from a surface (e.g., tooth surface and/or dental prosthesis) under a stream of room temperature water, typically from a dental water-spray unit, within about 10 seconds, such that there is little or no residue remaining.

The try-in pastes of the present invention include one or more particulate materials that give pastes with good handling properties and that have optical properties similar to polymerized dental cements, typically, polymerized methacrylate-based permanent dental resin cements. Typically, the particulate material includes one or more pigment(s) and/or one or more filler(s). Preferably, the particulate material includes one or more pigment(s) and optionally one or more filler(s).

Generally, a single try-in paste has one corresponding dental cement. As used herein, a "corresponding" try-in paste is one that is appropriately matched to the dental cement with respect to its final polymerized shade (typically, color, and preferably color and opacity).

Preferably, particulate material (preferably, pigment(s) and optional filler(s)) is present in an amount to provide a try-in paste having a color that matches the color of a corresponding polymerized dental cement. As used herein, a color that "matches" is one that has a very good match between $L^*$, $A^*$, and $B^*$ in the CIE color space (described in greater detail in the Examples Section), and preferably demonstrates a Delta $E^*$ of three units or less when compared to a corresponding polymerized dental cement.

More preferably, particulate material preferably, pigment(s) and optional filler(s)) is present in an amount to provide a try-in paste having an opacity that matches the opacity of a corresponding polymerized dental cement. As used herein, an opacity (i.e., Contrast Ratio or CR) (described in greater detail in the Examples Section) that "matches" a polymerized dental cement is one that has a very good CR match, and preferably demonstrates a Delta CR of about five units or less when compared to a corresponding polymerized dental cement.

The pigments may be colored (including black) pigments or white pigments. Preferably, to provide the desired shade match, the total amount of colored pigment used is at least about 0.001 weight percent (wt- %). Preferably, to provide the desired shade match, the total amount of colored pigment (s) used is no greater than about 0.1 wt- %. More preferably, these colored pigments are pure primary colors, i.e., red, yellow, and blue. Those skilled in the art will recognize this difficult challenge is made easier if the pigments are pure or nearly pure primary colors. In addition, a black pigment typically is preferred. Typically, a white pigment can be used in an amount of up to about 5 wt-%. These weight percentages are based on the total weight of the try-in paste.

Suitable pigments are those typically used in dental applications, and are preferably FDA approved. Examples of suitable colored (including black) pigments include the metal oxides such as iron oxides, aluminum oxides, copper oxides, chromium oxides, cobalt oxides, and ruthenium oxides. In addition, mixed metal oxides, i.e., spinels, and metal salts can be utilized as potentially suitable pigments. The preferred white pigments are the oxides of titanium.

Preferably, to provide the desired handling properties and shade match, the total amount of filler used is at least about 5 wt-%. Typically, to provide the desired handing properties and shade match, the total amount of filler used is no greater than about 50 wt-%, and preferably, no greater than about 20 wt-%. These weight percentages are based on the total weight of the try-in paste.

Suitable fillers are those typically used in dental applications and can be selected from any material suitable for use in medical applications. The fillers can be finely divided and preferably have a maximum particle diameter less than about 50 micrometers and an average particle diameter less than about 10 micrometers. The fillers can have a unimodal or polymodal (e.g., bimodal) particle size distribution. The fillers can be inorganic materials or crosslinked organic materials that are insoluble in the PEG components. Preferred fillers are white or nearly white. If a filler contains, for example, any red, yellow, or blue color, the task of obtaining color and opacity matching is made more difficult.

Suitable inorganic fillers are naturally occurring or synthetic materials such as quartz, nitrides (e.g., silicon nitride), zirconia-silica, glasses derived from, e.g., Ce, Sb, Sn, Zr, Sr, Ba, and Al. Other glasses include colloidal silica, feldspar, borosilicate glass, kaolin, talc, titania, and zinc glasses. Also suitable are the radiopaque, Zr—Si sol-gel fillers such as those described in U.S. Pat. No. 4,503,169 (Randklev) and submicron silica (e.g., pyrogenic silicas such as the AEROSIL series OX 50, 130, 150, and 200 silicas commercially available from Degussa Co., Germany and CAB-O-SIL M5 silica sold by Cabot Corp., Tuscola, Ill.). Optionally, the surface of the filler particles may be treated with a surface treatment, such as a silane coupling agent, as disclosed in U.S. Pat. No. 6,030,606 (Holmes).

Suitable non-reactive organic fillers include filled or unfilled pulverized polycarbonate, polyepoxides, and the like. Mixtures of the non-reactive organic fillers can also be used.

Those skilled in the art will recognize that both fillers and pigments add opacity to the paste formulations and care must be taken in choosing the proper amounts of filler, colored, black, and white pigments to achieve both color and opacity matching. Also, various combinations of fillers and pigments can be used to achieve the desired result.

The try-in (i.e., trial) paste compositions of this invention include a relatively low molecular weight (MW) polyalkylene glycol, preferably a polyethylene glycol (PEG), that is liquid at room temperature (i.e., about 20° C. to about 25°

C.) and a higher MW polyalkylene glycol, preferably a polyethylene glycol (PEG) that is solid at room temperature. Suitable polyalkylene glycols include polyethylene glycols, polypropylene glycols, and copolymers thereof. Mixtures of low MW liquid polyalkylene glycols and mixtures of high MW solid polyalkylene glycols can be used if desired. It is envisioned that a low MW polyethylene glycol can be mixed with a high MW polypropylene glycol.

Preferably, suitable liquid PEG's have a weight average MW of no greater than about 600 grams/mole (g/mol), and more preferably, no greater than about 400 g/mol. Preferably, suitable liquid PEG's have a weight average MW of at least about 100 g/mol, and more preferably, at least about 200 g/mol. Preferably, suitable solid PEG's have a weight average MW of at least about 700 g/mol, more preferably, at least about 1,000 g/mol, and most preferably, at least about 1,400 g/mol. Preferably, suitable solid PEG's have a weight average MW of no greater than about 20,000 g/mol, and more preferably, no greater than about 4,000 g/mol.

The ratio of liquid PEG and solid PEG is selected to provide a paste having the desired handling characteristics, as evidenced by a consistency of about 20 millimeters (mm) to about 50 mm as defined by the consistency test specified in ISO 4049 "Resin-based Dental Luting Material", Third Edition, published Jul. 15, 2000. Consistencies thicker than about 20 mm suffer from difficulty in dispensing and poor handling properties while consistencies thinner than about 50 mm suffer from excessive slump and runniness and an inability to hold a dental prosthesis in place for visual inspection.

Typically, the desired ratio for any one formulation depends on the particular MW of the liquid and solid PEG's. This can be determined by one of skill in the art without undue experimentation. In general, a weight ratio of liquid to solid PEG of at least about 1/1 is preferred, with a ratio of at least about 2/1 being more preferred. Also, a weight ratio of liquid to solid PEG of no greater than about 10/1 is preferred, with a ratio of no greater than about 5/1 being more preferred.

A particularly preferred paste includes a ratio of about 2.0–4.0 parts of a 200–400 MW liquid PEG to about 1.0 part of a 1,400–3,500 MW solid PEG, and more preferably, to about 1.0 part of a 2,000–3,500 MW solid PEG.

Preferably, the mixture of liquid and solid PEG's is heated until the solid PEG has melted and dissolved in the liquid PEG, and subsequently cooled with mixing. In this way, a creamy, homogeneous paste is typically obtained. If the heated mixture is cooled without mixing, a dispersion of solidified particles of high MW PEG in liquid PEG may be obtained. Pastes of this type are not suitably homogeneous, i.e., the naked eye can identify individual particles of solidified high MW PEG in a liquid low MW PEG.

Subsequent to the cooling cycle, fillers and/or pigments can be added to give a match between the shade (e.g., color and opacity) of the try-in paste and a final polymerized cement conventionally used in bonding a dental prosthesis. It is generally desirable to use pigments and fillers, if used, of a type that are similar to the cement being matched. In general, a color difference, Delta E*, of three units or less is considered to be an excellent match and difficult to discern a color difference.

The Examples Section describes six different try-in paste formulations (Trial Pastes A-F) and six different cement formulations (Cements A-F) corresponding to the same shade. Table 3 shows the computer results of the shade match obtained between the try-in pastes and their corresponding polymerized cements with color comparisons reported as Delta E* and opacity comparisons reported as Delta CR. These results are significantly better than many other conventional bonding systems, which can have Delta E* values of 12 and higher for some colors.

The present invention also provides a kit for selecting a dental cement for bonding a dental prosthesis to a tooth of a patient. The kit includes one or more dental cements and one or more try-in pastes of the present invention, wherein each dental cement has a corresponding shade-matched try-in paste. Typically, there is a translucent shade for use where the prosthesis provides the desired esthetics and no color shifting is necessary. If masking or shade adjustment is required, several other shades of try-in pastes and cements can be provided, including white, yellow, and dark shades. The kit will often also include a syringe that allows for easy and direct placement of the paste onto the prosthesis.

The dental cements can be resin cements, ionomeric cements, or resin-modified ionomeric cements. Preferably, the present try-in pastes are used to match the optical properties of (meth)acrylate-based resin cement. Suitable examples include a cement commercially available under the trade designations 3M ESPE RelyX Veneer Cement (3M Co., St. Paul, Minn.), CALIBRA (Dentsply, York, Pa.), VARIOLINK II (Ivoclar Vivadent, Amherst, N.Y.), and NEXUS (Kerr, Orange, Calif.).

The present invention also provides a method of selecting a dental cement for bonding a dental prosthesis to a tooth of a patient. The method includes: selecting a first try-in paste; applying the dental prosthesis to the tooth of the patient using the first try-in paste; comparing the shade of the dental prosthesis and the first try-in paste to the shade of the other teeth of the patient to determine if there is an appropriate shade match; removing the first try-in paste; and bonding the dental prosthesis to the tooth using a corresponding dental cement. As used herein, an "appropriate match" between the prosthesis/try-in paste and the other teeth of the patient occurs upon visual inspection and is defined as an esthetic result that is acceptable to the patient and dentist.

Comparing the shade includes comparing the color of the dental prosthesis and try-in paste to the color of the other teeth of the patient. Preferably, comparing the shade also includes comparing the opacity of the dental prosthesis and try-in paste to the opacity of the other teeth of the patient. Preferably, the method further includes selecting a different try-in paste if the shade match using the first try-in paste is not appropriate. This can be repeated numerous times until the appropriate shade match between the try-in paste and overlying prosthesis with the other teeth of the patient is obtained.

EXAMPLES

The following examples are given to illustrate, but not limit, the scope of this invention. Unless otherwise indicated, all parts and percentages are by weight and all molecular weights are weight average molecular weight.

Test Methods
PEG Blend Composition Stability

A small amount of PEG blend, typically 2–3 grams (g), was placed in a vial and placed in an oven at 37° C. and/or 45° C. overnight, about 12–18 hours. The samples were removed from the oven and immediately inspected visually for any evidence of melting or obvious changes in sample homogeneity. For details of "stability" results see Table 1.

Color and Opacity Measurement

All cement and try-in (i.e., trial) paste CIE L* A* B* color and opacity measurements were made in a single test on a Ultrascan XE Color Spectrophotometer (Hunter Associates Laboratory, Inc., Reston, Va.) with Universal Version 3.73 software operating in Opacity Y mode using default settings and wide area view. Opacity is defined as the contrast ratio (CR) obtained by this test.

Color and opacity measurements of trial paste samples were made by the following procedure. Two glass microscope slides (75 mm×50 mm×1.0 mm; Coming, Corning, N.Y.) were taped together along one of the long axis with a 1–mm gap to form a hinged sandwich configuration. The sandwich was laid open on a laboratory scale and two pieces of polyester film were placed on each face of the open glass sandwich. A stainless steel ring mold with an interior dimension of 31 mm and thickness of 1.00 mm was placed on one face of the glass/film sandwich. A sample (1.05–1.15 g) of trial paste was placed into the center of the ring mold taking care to avoid incorporation of any air bubbles. The sandwich was closed and a 1–kg weight was applied for about 10 seconds. The sample was placed in the Ultrascan XE to obtain L*, A*, and B* color coordinates and opacity (contrast ratio).

Color and opacity measurements of cement samples were made using the above procedure, except with the following changes. A sample (1.50–1.60 g) of cement was used and, following the application of the 1–kg weight, the sample was light-cured for 90 seconds per side using a XL 3000 dental curing unit (3M Co., St. Paul, Minn.). Heavy finger pressure was applied to keep the sandwich clamped together tightly at all times during light curing and data acquisition. This was necessary to prevent delamination of the polyester film from the cured cement. Delamination of the film from the cement would give rise to the formation of an air gap between the cement and film and could introduce error into the color spectrophotometer results.

Calculation of Delta E*. The comparison of color matching between trial paste and cured cement samples was obtained by calculating Delta E*, a calculation for determining the distance between two points in the L*, A*, B* color coordinate space. Delta E*=Square Root $((L^*_T - L^*_C)^2 + (A^*_T - A^*_C)^2 + (B^*_T - B^*_C)^2)$, where $L^*_T$, $A^*_T$, and $B^*_T$ are the L*, A*, and B* color coordinates of the trial paste samples and $L^*_C$, $A^*_C$, and $B^*_C$ are the L*, A*, and B* color coordinates of the cured cement samples. In general, a color difference (Delta E*) of less than three units is considered to be an excellent match and difficult to discern a color difference by visual observation.

Calculation of Delta CR. The comparison of opacity matching between trial paste and cured cement was obtained by taking the absolute value of the difference between the cement contrast ratio and the trial paste contrast ratio. An opacity difference less than about 5.0 is considered to be an excellent match and difficult to discern an opacity difference by visual observation.

| Abbreviations/Definitions | |
|---|---|
| BHT | 2,6-Di-tert-butyl-4-methylphenol (Sigma-Aldrich Fine Chemicals, St. Louis, MO) |
| Bis-GMA | Bisphenol A diglycidyl dimethacrylate (CAS number 1565-94-2) |
| CPQ | Camphorquinone (Sigma-Aldrich) |
| EDMAB | Ethyl 4-dimethylaminobenzoate (Sigma-Aldrich) |
| IEM | 2-Isocyanatoethyl methacrylate (Sigma-Aldrich) |

-continued

| Abbreviations/Definitions | |
|---|---|
| TONE 0230 Diol | α,ω-Hydroxy-terminated caprolactone (Union Carbide, Danbury, CT) |
| TONE 0230-IEM | Reaction product between TONE 230 Diol and IEM; prepared as described in U.S. patent application Ser. No. 08/896,549 (Aasen et al.), July 18, 1997 |
| TEGDMA | Triethylene glycol dimethacrylate (Sartomer Co.; West Chester, PA) |
| DPIHFP | Diphenyliodonium HFP (Johnson Matthey, Alpha Aesar Division, Ward Hill, NJ |
| NORBLOCK 7966 | 2-(2-Hydroxy-5-Methacrylyoxyethylphenyl)-2H-Benzotriazole (Janssen Pharmaceutica, Titusville, NJ) |
| PEG-300 | Liquid Polyethylene glycol; MW about 300 (Union Carbide Corp., New Milford, CT) |
| PEG-400 | Liquid Polyethylene glycol; MW about 400 (Union Carbide Corp., New Milford, CT) |
| PEG-1450 | Solid Polyethylene glycol; MW about 1450 (Union Carbide Corp., New Milford, CT) |
| PEG-3350 | Solid Polyethylene glycol; MW about 3350 (Union Carbide Corp., New Milford, CT) |
| A-174 Silane | Silquest A-174 Silane (Crompton Corp., Friendly, WV) |

Starting Materials

Preparation of Zirconia-Silica (Zr-Si) Filler

Radiopaque Zr-Si filler was prepared as described in U.S. Pat. No. 4,503,169 (Randklev).

Preparation of Silane-Treated Zr-Si Filler

Silane-treated Zr-Si filler was prepared as described in U.S. Pat. No. 6,030,606 (Holmes).

Preparation of Silane-Treated OX-50 Filler

A silanol solution was prepared by mixing together 16.48 parts of A-174 silane, 10.99 parts of methanol, 1.49 parts of acetic acid, and 2.39 parts of deionized water. During mixing the silanol solution was kept in a temperature range of 20° C. to 30° C. Colloidal silica (OX-50) (68.66 parts). (Degussa Corp, Germany) was charged to a V-blender and, with mixing, the silanol solution was added to the V-blender over the course of 30 minutes. The resulting treated powder was discharged from the V-blender into plastic-lined trays, dried for three hours and 45 minutes at 67° C., and then further dried for one hour and 15 minutes at 100° C.

Preparation of Pigment Pastes

Raw yellow (Harcros Pigments Inc., Easton, Pa.), black (Elementis Pigments Inc., Fairview, Ill.), red (Wamer-Jenkinson Cosmetic Colors, S. Plainfield, N.J.), and white (Daicolor-Pope, Inc., Clifton, N.J.) pigments were individually screened through a 100-micron mesh screen. The pigments were individually combined with PEG Blend A (Example 27) in a plastic cup closed with a screw-cap lid and mixed in a high speed mixer at 2500 rpm for 1 minute. The sides and bottom of the cup were scraped with a wooden tongue blade and the mixing repeated for two additional 1-minute cycles at 2500 rpm to afford 5% yellow, 5% black, 5% red, and 20% white (Micro $TiO_2$) blended pigments.

Preparation of Liquid Pigments

Raw yellow, black, and red pigments were individually screened through a 100-micron mesh screen. The pigments were individually dispersed in bis-GMA to afford 5% yellow, 5% black, and 5% red liquid pigments.

Preparation of Activated Resin

TEGDMA (37.930 parts) and 90/10 Bis-GMA/TEGDMA (47.419 parts) were placed in a large plastic pail and heated in an oven at 55–60° C. for 3 hours. TONE 0230-IEM (13.320 parts) was added and the resulting suspension stirred slowly with an overhead stirrer until all the solid was dissolved, about 5 hours. EDMAB (0.313 part), DFIHFP (0.313 part), and CPQ (0.078 part) were combined, ground into a fine powder with a mortar and pestle, and added to the solution with stirring for an additional hour at 55–60° C. NORBLOCK 7966 (0.627 part) was added to the solution with stirring for an additional 2 hours at 30–35° C. The warm solution was screened through a 100-micron mesh screen to yield a viscous, yellow liquid designated as the Activated Resin.

Preparation of Translucent Cement A

The Activated Resin (34.000 parts), Silane-Treated Zr-Si Filler (59.400 parts), and Silane-Treated OX-50 Filler (6.600 parts) were added to a double planetary mixer fitted with vacuum capabilities. A vacuum of less than 200 mm Hg was pulled for one minute and the mixer pressurized to 3.4 KPa (0.5 psi) with a 90/10 helium/oxygen mixture. The resulting mixture was mixed at 100 rpm for 5–10 minutes, the pressure was released, and the sides and bottom of the mixer were scraped with a plastic spatula. The cement was mixed for two additional 15-minute cycles at 175 rpm following the vacuum/pressurization procedure just described to afford a homogeneous paste-like cement designated Translucent Cement A.

Preparation of Light Yellow Cement B

Translucent Cement A (99.934 parts), 5% Yellow Liquid Pigment (0.036 part), and 5% Black Liquid Pigment (0.030 part) were added to a double planetary mixer and subjected to the vacuum/pressurization procedure described for the Translucent Cement A (except a mixing speed of 40 rpm was used) to afford a homogeneous paste-like cement designated Light Yellow Cement B.

Preparation of Yellow Opaque Cement C

Translucent Cement A (99.057 parts), 5% Yellow Liquid Pigment (0.327 part), 5% Black Liquid Pigment (0.032 part), 5% Red Liquid Pigment (0.002 part), and Micro $TiO_2$ (0.582 part) were added to a double planetary mixer and subjected to the vacuum/pressurization procedure described for the Translucent Cement A (except a mixing speed of 40 rpm was used). The Micro $TiO_2$ was screened through a 100-micron mesh screen before being added to the mixer. The resulting homogeneous paste-like cement was designated Yellow Opaque Cement C.

Preparation of Opaque/Dark Cement D

CPQ (0.027 part), EDMAB (90.230 parts), and DPIHFP (0.105 part) were combined, ground into a fine powder with a mortar and pestle, and added to the Activated Resin (33.145 parts) in a plastic pail fitted with an overhead stirrer. The suspension was stirred until all solids were dissolved (about 1 hour) and screened through a 100-micron mesh screen. This solution was transferred to a double planetary mixer and Silane-Treated Zr-Si (58.534 parts), Silane-Treated OX-50 Filler (6.502 parts), Micro $TiO_2$ (0.714 part), 5% Yellow Liquid Pigment (0.689 part), and 5% Black Liquid Pigment (0.054 part). The Micro $TiO_2$ was screened through a 100-micron mesh screen before being added to the mixer. A homogeneous paste-like cement was obtained following one 5-minute and two 10-minute vacuum/pressurization mixing cycles as described above with mixing at 40 rpm. The paste was designated Opaque/Dark Cement D.

Preparation of White Cement E

Translucent Cement A (99.789 parts), 5% Yellow Liquid Pigment (0.019 part), 5% Black Liquid Pigment (0.006 part), 5% Red Liquid Pigment (0.006 part), and Micro $TiO_2$ (0.180 part) were added to a double planetary mixer and subjected to the vacuum/pressurization procedure described for the Translucent Cement A (except a mixing speed of 40 rpm was used). The Micro $TiO_2$ was screened through a 100-micron mesh screen before being added to the mixer. The resulting homogeneous paste-like cement was designated White Cement E.

Preparation of White Opaque Cement F

Translucent Cement A (99.205 parts), 5% Yellow Liquid Pigment (0.005 part), 5% Black Liquid Pigment (0.011 part), 5% Red Liquid Pigment (0.002 part), and Micro $TiO_2$ (0.777 part) were added to a double planetary mixer and subjected to the vacuum/pressurization procedure described for the Translucent Cement A (except a mixing speed of 40 rpm was used). The Micro $TiO_2$ was screened through a 100-micron mesh screen before being added to the mixer. The resulting homogeneous paste-like cement was designated White Opaque Cement F.

Examples 1–16

PEG Blend Compositions Without Mixing during Cooling Step

Predetermined amounts of a liquid PEG and a solid PEG were added to a small glass jar closed with a snap-on cap and heated in an oven at 60° C. until a clear solution was obtained, about 15–30 minutes. The jar was removed from the oven and allowed to cool to room temperature without mixing. The amounts (in parts by weight) of the PEGs used are shown in Table 1 along with an indication of blend stability at 37° C. and 45° C. as determined by the test method described herein. In each case (Examples 1–16), the resulting PEG blend was a milky-white paste-like mixture visually observed to lack homogeneity and to consist of white particles dispersed in a clear liquid.

Examples 17–26

PEG Blend Compositions With Mixing during Cooling Step

Predetermined amounts of a liquid PEG and a solid PEG were blended and processed as described for Examples 1–16, except that the heated clear solution was mixed in a double planetary mixer under vacuum during the time that it was allowed to cool to room temperature. The amounts (in parts by weight) of the PEGs used are shown in Table 1 along with an indication of blend stability at 37° C. and 45° C. as determined by the test method described herein. Additionally, as shown in Table 1, predetermined amounts of Zr-Si Filler and $TiO_2$ Pigment were optionally added after cooling to room temperature. In each case (Examples 17–26), the resulting PEG blend was a milky-white paste visually observed to be homogeneous and was stable at 37° C. and 45° C. as determined by the test method described herein.

TABLE 1

| Ex. | Liquid PEG MW | Liquid PEG Parts | Solid PEG MW | Solid PEG Parts | Zr—Si Filler Parts | $TiO_2$ Pigment Parts | Stable 37° C. | Stable 45° C. |
|---|---|---|---|---|---|---|---|---|
| 1 | 300 | 2.5 | 1450 | 1.0 | 0.0 | 0.0 | Yes | No |
| 2 | 300 | 2.7 | 1450 | 1.0 | 0.0 | 0.0 | Yes | No |
| 3 | 300 | 3.0 | 1450 | 1.0 | 0.0 | 0.0 | Yes | No |
| 4 | 300 | 3.3 | 1450 | 1.0 | 0.0 | 0.0 | Yes | No |
| 5 | 300 | 4.0 | 1450 | 1.0 | 0.0 | 0.0 | Yes | No |
| 6 | 300 | 2.0 | 3350 | 1.0 | 0.0 | 0.0 | Yes | Yes |
| 7 | 300 | 2.5 | 3350 | 1.0 | 0.0 | 0.0 | Yes | Yes |
| 8 | 300 | 3.0 | 3350 | 1.0 | 0.0 | 0.0 | Yes | Yes |

TABLE 1-continued

| | Liquid PEG | | Solid PEG | | Zr—Si Filler | TiO$_2$ Pigment | Stable | |
|---|---|---|---|---|---|---|---|---|
| Ex. | MW | Parts | MW | Parts | Parts | Parts | 37° C. | 45° C. |
| 9 | 300 | 4.0 | 3350 | 1.0 | 0.0 | 0.0 | Yes | Yes |
| 10 | 300 | 5.0 | 3350 | 1.0 | 0.0 | 0.0 | Yes | Yes |
| 11 | 300 | 7.0 | 3350 | 1.0 | 0.0 | 0.0 | Yes | Yes |
| 12 | 300 | 10.0 | 3350 | 1.0 | 0.0 | 0.0 | Yes | Yes |
| 13 | 400 | 3.0 | 3350 | 1.0 | 0.0 | 0.0 | Not Tested | |
| 14 | 400 | 4.0 | 3350 | 1.0 | 0.0 | 0.0 | Not Tested | |
| 15 | 400 | 5.0 | 3350 | 1.0 | 0.0 | 0.0 | Not Tested | |
| 16 | 400 | 6.0 | 3350 | 1.0 | 0.0 | 0.0 | Not Tested | |
| 17 | 300 | 2.5 | 3350 | 1.0 | 0.0 | 0.0 | Yes | Yes |
| 18 | 300 | 13.6 | 3350 | 5.4 | 1.0 | 0.0 | Yes | Yes |
| 19 | 300 | 3.0 | 3350 | 1.0 | 0.0 | 0.0 | Yes | Yes |
| 20 | 300 | 14.3 | 3350 | 4.8 | 1.0 | 0.0 | Yes | Yes |
| 21 | 300 | 4.0 | 3350 | 1.0 | 0.0 | 0.0 | Yes | Yes |
| 22 | 300 | 15.2 | 3350 | 3.8 | 1.0 | 0.0 | Yes | Yes |
| 23 | 300 | 73.1 | 3350 | 20.9 | 5.0 | 1.0 | Yes | Yes |
| 24 | 300 | 73.5 | 3350 | 21.0 | 5.0 | 0.5 | Yes | Yes |
| 25 | 300 | 73.7 | 3350 | 21.1 | 5.0 | 0.2 | Yes | Yes |
| 26 | 300 | 73.8 | 3350 | 21.1 | 5.0 | 0.1 | Yes | Yes |

Example 27

PEG Blend A

PEG 300 (71.429 parts) and PEG 3350 (28.571 parts) were added to a water-jacketed double planetary mixer fitted with vacuum capabilities. The resulting mixture was stirred for about 20 minutes at 100 rpm with the water-jacket temperature at 66° C. to afford a clear solution. Heating was discontinued and the water-jacket was cooled to 10° C. while mixing at 100 rpm and pulling a vacuum less than 200 mm Hg until the batch temperature was less than 25° C., about 6 hours. A homogeneous milky-white paste was obtained.

Example 28

Translucent Trial Paste A

The PEG Blend A (89.992 parts), Zr-Si Filler (9.975 parts), 5% Yellow Pigment Paste (0.028 part), and 5% Black Pigment Paste (0.005 part) were added to a double planetary mixer and mixed for 5 minutes at 40 rpm under vacuum less than 200 mm Hg. The sides and bottom of the mixer were scraped with a plastic spatula. This procedure was repeated for two additional 10-minute mixing cycles at 40 rpm and vacuum less than 200 mm Hg to afford a homogeneous paste designated Translucent Trial Paste A.

Example 29

Light Yellow Trial Paste B

The Translucent Trial Paste A (99.884 parts), 5% Yellow Pigment Paste (0.083 part), and 5% Black Pigment Paste (0.033 part) were added to a double planetary mixer and mixed for 5 minutes at 40 rpm under vacuum less than 200 mm Hg. The sides and bottom of the mixer were scraped with a plastic spatula. This procedure was repeated for two additional 10-minute mixing cycles at 40 rpm and vacuum less than 200 mm Hg to afford a homogeneous paste designated Light Yellow Trial Paste B.

Example 30

Yellow Opaque Trial Paste C

The Translucent Trial Paste A (98.070 parts), 20% Micro TiO$_2$ (1.513 parts), 5% Yellow Pigment Paste (0.344 part), 5% Black Pigment Paste (0.072 part), and 5% Red Pigment Paste (0.001 part) were added to a double planetary mixer and mixed for 5 minutes at 40 rpm under vacuum less than 200 mm Hg. The sides and bottom of the mixer were scraped with a plastic spatula. This procedure was repeated for two additional 10-minute mixing cycles at 40 rpm and vacuum less than 200 mm Hg to afford a homogeneous paste designated Yellow Opaque Trial Paste C.

Example 31

Opaque/Dark Trial Paste D

The Translucent Trial Paste A (96.735 parts), 20% Micro TiO$_2$ (2.412 parts), 5% Yellow Pigment Paste (0.736 part), 5% Black Pigment Paste (0.106 part), and 5% Red Pigment Paste (0.011 part) were added to a double planetary mixer and processed as described for Yellow Opaque Trial Paste C to afford a homogeneous paste designated Opaque/Dark Trial Paste D.

Example 32

White Trial Paste E

The Translucent Trial Paste A (99.286 parts), 20% Micro TiO$_2$ (0.662 part), 5% Yellow Pigment Paste (0.031 part), 5% Black Pigment Paste (0.015 part), and 5% Red Pigment Paste (0.006 part) were added to a double planetary mixer and processed as described for Yellow Opaque Trial Paste C to afford a homogeneous paste designated White Trial Paste E.

Example 33

White Opaque Trial Paste F

The Translucent Trial Paste A (92.174 parts), 20% Micro TiO$_2$ (7.684 parts), 5% Yellow Pigment Paste (0.092 part), 5% Black Pigment Paste (0.046 part), and 5% Red Pigment Paste (0.004 part) were added to a double planetary mixer and processed as described for Yellow Opaque Trial Paste C to afford a homogeneous paste designated White Opaque Trial Paste F.

Evaluation of Trial Paste and

Cured Cement Samples for Color and Opacity Differences

Color (Delta E*) and Opacity (Delta CR) differences between the cement samples (Cements A-F) and the trial paste samples (Trial Pastes A-F, Examples 28–33) were determined according to the Color Measurement Test Method described herein and the results are provided in Table 3. Also provided in Table 3 are the color differences (Delta E*) between cement and trial paste samples for the commercial dental products CALIBRA (Dentsply, York, Pa.), VARIOLINK II (Ivoclar Vivadent, Amherst, N.Y.), and NEXUS (Kerr, Orange, Calif.). It can be concluded from the results of Table 3 that the trial paste samples of the present invention provide an excellent color match to their corresponding cured cement samples (all with Delta E* values less than 3 units), whereas the comparative commercial samples typically gave color matches (Delta E*) significantly above 3 units.

TABLE 3

| Source of Samples | Shade of Cement and Corresponding Trial Paste Samples | Delta E* | Delta CR |
|---|---|---|---|
| Cements A–F | Translucent | 0.78 | 4.4 |
| Trial Pastes A–F | Light Yellow | 1.99 | 2.5 |
| | Yellow Opaque | 2.53 | 5.1 |
| | Opaque/Dark | 0.66 | 0.6 |
| | White | 1.81 | 1.5 |
| | White Opaque | 1.73 | 5.8 |
| CALIBRA | Translucent | 15.65 | — |
| | Light | 8.31 | — |
| | Medium | 8.49 | — |
| | Dark | 5.68 | — |
| | Opaque | 6.88 | — |
| VARIOLINK II | Transparent | 8.11 | — |
| | White | 3.35 | — |
| | Yellow | 4.32 | — |
| | Brown | 1.45 | — |
| | Bleach | 4.40 | — |
| | White Opaque | 2.17 | — |
| NEXUS | Neutral | 8.00 | — |
| | Light | 3.86 | — |
| | Dark | 2.09 | — |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not to be unduly limited to the illustrative embodiments and examples set forth herein and that such examples and embodiments are presented by way of example only with the scope of the invention intended to be limited only by the claims set forth herein as follows.

What is claimed is:

1. A method of selecting a dental cement for bonding a dental prosthesis to a tooth of a patient, the method comprising:
    selecting a first try-in paste;
    applying the dental prosthesis to the tooth of the patient using the first try-in paste;
    comparing the shading of the dental prosthesis and the first try-in paste to the shading of the other teeth of the patient to determine if there is an appropriate match;
    removing the first try-in paste; and
    bonding the dental prosthesis to the tooth using a corresponding dental cement;
    wherein the try-in paste comprises:
        a polyethylene glycol that is liquid at room temperature and that has a weight average molecular weight of about 100 g/mol to about 600 g/mol;
        a polyethylene glycol that is solid at room temperature and that has a weight average molecular weight of about 700 g/mol to about 20,000 g/mol; and
        particulate material;
        wherein the weight ratio of liquid to solid polyethylene glycol is about 1/1 to about 10/1; and
        wherein the particulate material is present in an amount to provide a try-in paste having a shading that matches the shading of a corresponding polymerized dental cement.

2. The method of claim 1 wherein the try-in paste is removable from a surface under a stream of room temperature water from a dental water-spray unit within about 10 seconds.

3. The method of claim 1 wherein the particulate material comprises a pigment.

4. The method of claim 3 wherein the pigment is a colored pigment.

5. The method of claim 4 wherein the colored pigment is present in an amount of about 0.001 wt-% to about 0.1 wt-%.

6. The method of claim 3 wherein the pigment is a white pigment.

7. The method of claim 6 wherein the white pigment is present in an amount of up to about 5 wt-%.

8. The method of claim 1 wherein the particulate material comprises a filler.

9. The method of claim 8 wherein the filler is present in an amount of about 5 wt-% to about 50 wt-%.

10. The method of claim 1 wherein comparing the shading includes comparing the color and opacity of the dental prosthesis and the try-in paste to the color and opacity of the other teeth of the patient.

11. The method of claim 1 further comprising selecting a different try-in paste if the match using the first try-in paste is not appropriate.

12. The method of claim 1 wherein the particulate material is present in the try-in paste in an amount to provide a try-in paste having a shading that matches the shading of a corresponding polymerized dental cement such that the color match is within a Delta E* of three units or less.

13. The method of claim 1 wherein the particulate material is present in the try-in paste in an amount to provide a try-in paste having an opacity that matches the opacity of a corresponding polymerized dental cement within a Delta Contrast Ratio (CR) of five units or less.

* * * * *

UNITED STATES PATENT AND TRADEMARK OFFICE
CERTIFICATE OF CORRECTION

PATENT NO.     : 6,579,919 B2
DATED          : June 17, 2003
INVENTOR(S)    : Konings, Mark S.

It is certified that error appears in the above-identified patent and that said Letters Patent is hereby corrected as shown below:

Title page,
Item [56], References Cited, FOREIGN PATENT DOCUMENTS, please delete "1/1993" and insert in place thereof -- 1/1983 --.

Column 3,
Line 56, please insert -- ( -- following "material".

Column 7,
Line 11, please delete "Coming" and insert in place thereof -- Corning --.

Column 8,
Line 46, please delete "Wamer" and insert in place thereof -- Warner --.

Signed and Sealed this

Twenty-seventh Day of July, 2004

JON W. DUDAS
*Acting Director of the United States Patent and Trademark Office*